United States Patent [19]

Abraham

[11] 4,269,189

[45] May 26, 1981

[54] SKIN CONDUCTING ELECTRODE ASSEMBLY

[75] Inventor: William W. Abraham, New Hartford, N.Y.

[73] Assignee: Consolidated Medical Equipment Inc., Utica, N.Y.

[21] Appl. No.: 55,811

[22] Filed: Jul. 9, 1979

[51] Int. Cl.³ ............................................. A61B 17/39
[52] U.S. Cl. ................................ 128/303.13; 128/798
[58] Field of Search ............................... 128/639–641, 128/644, 303.13, 783, 798, 802, 803

[56] References Cited

U.S. PATENT DOCUMENTS

| 3,387,608 | 6/1968 | Figar | 128/640 |
| 3,774,592 | 11/1973 | Lahr | 128/640 |
| 4,117,846 | 10/1978 | Williams | 128/303.13 |
| 4,161,174 | 7/1979 | Mercuri | 128/641 |

FOREIGN PATENT DOCUMENTS 2239596  2/1974  Fed. Rep. of Germany ............ 128/798
166447  10/1962  U.S.S.R. .................................. 128/640

*Primary Examiner*—Lee S. Cohen
*Attorney, Agent, or Firm*—Larson, Taylor and Hinds

[57] ABSTRACT

A disposable skin conducting electrode assembly and electrode is disclosed for use on a patient wherein the electrode assembly comprises a gel pad, an electrode and an adhesive pad. The electrode is a thin conductive plate containing an interior area or aperture. In one particular embodiment, the electrode is doughnut shaped. The gel pad covers one side of the conductive plate and is similarly shaped. The adhesive pad covers the other side of the electrode and extends over the aperture and beyond the periphery of the gel pad. The adhesive provides good contact around the external edges of the gel pad, and due to the aperture, the adhesive pad provides good adhesive contact to the patient around internal edges of the gel pad as well. An external conductor is connectable to a conductive, single piece solid metal stud or post attached to the electrode and extending through an orifice in the adhesive pad.

7 Claims, 4 Drawing Figures

SKIN CONDUCTING ELECTRODE ASSEMBLY

FIELD OF THE INVENTION

This invention relates generally to a skin conducting electrode assembly and electrode, and more particularly, to a disposable skin electrode assembly providing good electrical contact with a patient so that the electrode assembly can be used as a return electrode during electrosurgery or as an active electrode for applying an electric current to a portion of a patient's body.

BACKGROUND OF THE INVENTION

As discussed in more detail in a previous U.S. Pat. No. 4,117,846, incorporated herein by reference, electrosurgery is the use of high frequency electrical current for cutting tissues and also for causing a coagulation of hemostasis of tissues. The basic mechanisms responsible for either the cutting or coagulation of the tissues is the production of heat either at the immediate site of the electrical arc or in adjacent tissues. If the electrode is small, the heating will be concentrated near the electrode's point of contact with a patient. Obviously, this is desired with an active electrode which is used to cause the cutting or coagulation of the patient. However, no tissue heating is desired near the point where the current leaves the patient at a return electrode or grounding pad electrode. Thus, the ground pad electrode should provide a low impedance and a low current density path for the return current. If the grounding pad does not provide good patient contact, burns can occur. Therefore, an adequate grounding pad which conforms to the patient and resists patient scretching is necessary in order to assure safe, burn-free electrosurgery.

There are numerous electrodes in the prior art, including those which were disclosed in the prior patent. In that patent, an electrode assembly is disclosed which has a series of projections around the periphery of a main electrode body. When this electrode assembly is placed on the patient, the adhesive pad makes contact with the patient around and within the recesses between the projections to provide good contact between the gel pad under the electrode and the patient's skin. It has also been disclosed in German Pat. No. 2,239,596 to Hetz to provide small recesses in a bare electrode so that the overlying adhesive tape fills these recesses and sticks to the skin of the patient. Small openings in a rubber-backed bare electrode have also been disclosed in U.S. Pat. No. 1,973,387 to Neymann et al, the number of openings being varied to increase or decrease the conductive area of the electrode.

While the '846 U.S. patent provides good contact for an elongate gel pad and electrode, the main body of the gel pad is still subject to some loose contact, as are the gel pads of other prior art patents.

SUMMARY OF THE INVENTION

In accordance with the present invention, a disposable skin conducting electrode assembly and electrode is provided which is used as a ground electrode pad on a patient undergoing electrosurgery. The present invention provides for greater leading edge contact to minimize heating of the area. In addition, the present invention provides for increased adhesion to the skin and a reduction in the "tenting" effect found in prior art electrodes.

In one embodiment of the present invention, the electrode is formed from a thin conductive plate having a circular aperture therein. This electrode is sandwiched between a gel pad which contacts the skin and also has a corresponding aperture, and an adhesive pad which extends beyond the gel pad and over the aperture to hold the electrode assembly in place and to provide good contact with the patient's skin along the edges of the gel pad. The circular pad gives equal current dispersion regardless of angle of placement of the pad in relation to the operating site. This is not true with conventional rectangular pads. A one-piece conductive post or stud is electrically connected to the electrode to provide an attachment point for a wire from an electrosurgery machine.

Other features and advantages of the present invention are stated in or apparent from the detailed description of the presently preferred embodiments of the invention found hereinbelow.

DETAILED DESCRIPTION OF THE PREFERRED EMBODIMENTS

It has been discovered during electrosurgery that surface current readily disperses laterally across a patient's skin and that there is extremely low impedance to this lateral current dispersal. It has also been discovered that the area of a plate electrode can be significantly reduced with almost negligible effect on the skin-conductor interface impedance so long as the perimeter or leading edges of the plate are not reduced in length. In addition, a negligible, if any, increase in electrical heating has been found.

Figure 1:
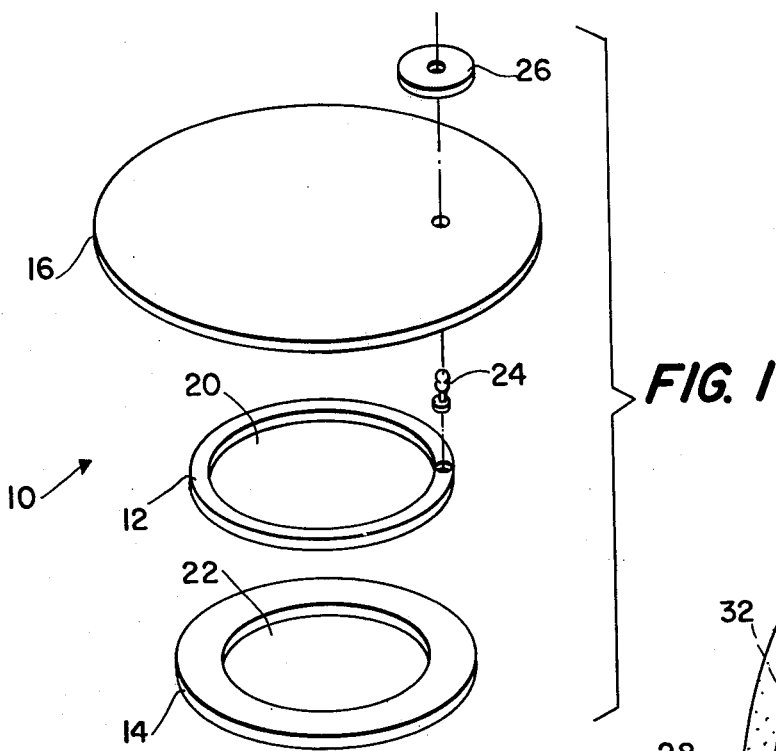
FIG. 1 is an exploded perspective view of the components of the skin conducting electrode assembly in accordance with a preferred embodiment of the present invention.
Figure 2:
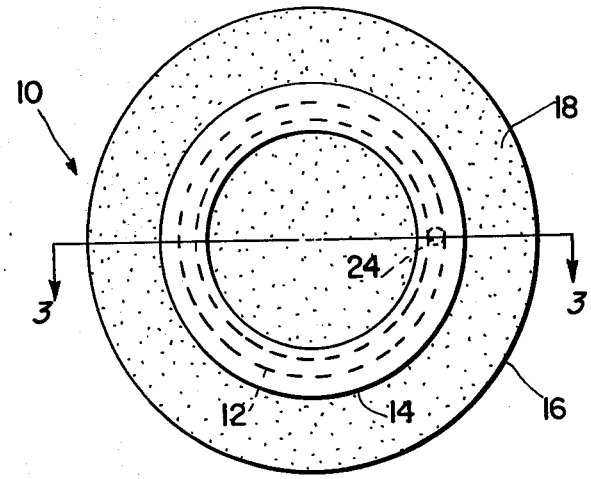
FIG. 2 is a bottom plan view of the skin conducting electrode assembly showing the hidden components in phantom.
Figure 3:
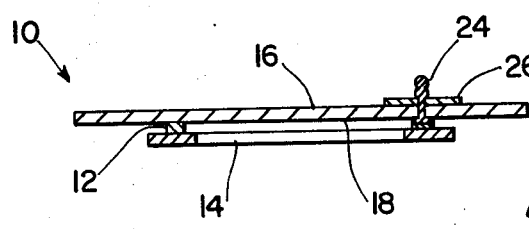
FIG. 3 is a cross-sectional side view taken along the line 3—3 in FIG. 2.

With reference now to the drawings in which like numerals represent like elements throughout the several views, a presently preferred embodiment of the present invention is depicted in FIGS. 1, 2 and 3 and comprises a disposable skin conducting electrode assembly 10 having an electrode 12 sandwiched between a gel pad 14 and an adhesive pad 16. The underside 18 of adhesive pad 16 is the adhesive side so that both electrode 12 and gel pad 14 adhere to adhesive pad 16. As shown, both electrode 12 and gel pad 14 are doughnut shaped, so that electrode 12 has an interior area or aperture 20 and gel pad 14 has an interior area or aperture 22. Gel pad 14 completely covers electrode 12 to prevent direct contact of electrode 12 with the skin of the patient. Adhesive pad 16 is similarly shaped like gel pad 14, but adhesive pad 16 has no aperture. It is within the scope of the present invention to provide and aperture within the adhesive pad 16. Such an opening would facilitate locating the pad over a sharp body contour. Thus, adhesive pad 16 covers both gel pad 14 and electrode 12, extending beyond the outer edges of gel pad 14. A metallic, one-piece stud or post 24 is fixedly mounted to the top surface of electrode 12 in electrical connection therewith. Metallic stud 24 extends through adhesive pad 16 and a retaining washer 26 is rigidly mounted around metallic stud 24 on top of adhesive pad 16.

As clearly shown in FIG. 1 and as shown in phantom in FIG. 3, electrode 12 and gel pad 14 are formed of concentric rings. By cutting away the interior areas of apertures 20 and 22, a significant savings in material can be achieved. Such a cutting away of the interior areas also increase the flexibility of the assembly. And because the interior area is bounded by the leading edge or interior edge of electrode 12 and gel pad 14, the interface impedance is only slightly less than that of a circular electrode having the same diameter and on cutouts. Additionally, the interior areas 20 and 22 provide an area of contact to the patient's skin for adhesive pad 16, so that good electrical contact of electrode 12 and gel pad 14 is assured along the leading edges. With such good contact to the skin, electrode assembly 10 provides a lower contact impedance, a cooler electrode, and one that can be placed closer to the operating site without regard to the angle of placement of the pad relative to the cutting site.

A suitable material for electrode 12 is 316 stainless steel having a thickness of one thousandth of an inch. Typically, the inside diameter of aperture 20 is one twentieth or greater than the outside diameter of electrode 20. Apertures 20 and 22 must also be large enough to ensure that the portion of adhesive pad 16 projecting through apertures 20 and 22 maintains positive contact with the patient. Gel pad 14 is made from a flexible cellular material impregnated with a conductive electrolyte solution, such as one sixteenth inch thick 100 cpi "Scott Foam". The adhesive for the adhesive underside 18 of adhesive pad 16 is selected from a group of adhesives that are medically compatible and are well known in the art. This adhesive is applied to one side of adhesive pad 16, and adhesive pad 16 is formed from a material such as one eighth inch thick 4 pound "White Foam" cross linked polyethylene. Together, electrode assembly 10 provides an air tight seal entirely around electrode 12 and gel pad 14 and prevents gel pad 14 from drying out.

In operation, the disposable skin conducting electrode assembly 10 functions in the following manner when it is used as a grounding pad electrode in electrosurgery. Generally, it is desirable to place the electrode assembly 10 as close to the operating sites as possible, usually the chest or back area. Thus, with the appropriate area chosen, the electrode assembly is attached to the skin by the adhesive underside 18 of adhesive pad 16. Even though the skin area may not be flat, the overlapping edges of adhesive pad 16 and the part of adhesive pad 16 inside of apertures 20 and 22 assure that good electrical contact is achieved along the leading edges of electrode 12 and gel pad 14. With a suitable lead (not shown) attached to metallic stud 24, the electrode assembly acts to provide a low impedance and low current density path for a return current. The return current is first picked up by gel pad 14 and transferred from gel pad 14 to electrode 12. From electrode 12, the return current travels along metallic stud 24 to the lead wire and back to the source (not shown).

Figure 4:
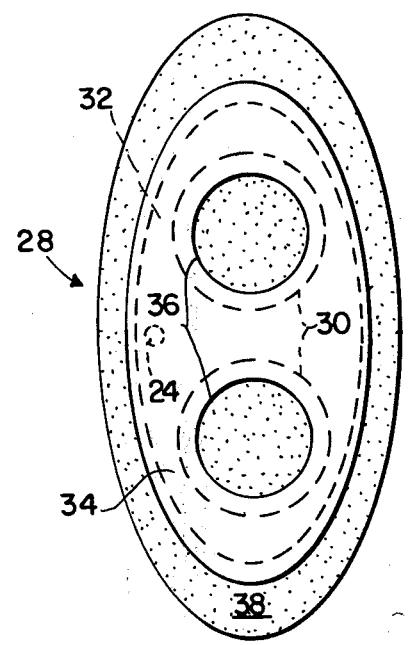
FIG. 4 is a bottom plan view of an alternative embodiment of the present invention showing the hidden components in phantom.

An alternative embodiment of the present invention is depicted in FIG. 4 and comprises an electrode assembly 28. In this embodiment, two apertures 30 are located in an oval shaped electrode 32. Electrode 32 is sandwiched between a gel pad 34 having two corresponding apertures 36 and an adhesive pad 38. Like the previous embodiment, gel pad 34 completely covers electrode 32, and adhesive pad 38 covers apertures 30 and 36 and extends beyond the outer edges of gel pad 34. A metallic stud 24 is also connected to electrode 32. In operation, the electrode assembly 12 functions the same as the above-described electrode assembly 10.

Other alternative embodiments of the invention should be apparent to those of ordinary skill in the art. For instance, rather than being a complete ring, the electrode could be an open ring of approximately 270°. Additionally, the particular shape of the apertures or the rest of the elements of the electrode assembly could be varied to suit particular needs. It is also possible to add scallops or the like, as described in the above-identified prior patent, to either or both of the interior and exterior edges of the electrode and the gel pad.

Although the invention has been described with respect to exemplary embodiments thereof, it will be understood by those of ordinary skill in the art that variations and modifications may be effected within the scope and spirit of the invention.

I claim:

1. A skin conducting electrode assembly for use on a patient comprising in combination,
   an electrode comprising a thin conductive plate containing a wholly enclosed interior aperture therein defined by an inner edge of the electrode, the shapes of both the outer edge of the electrode and the inner edge of the electrode being rounded;
   means for making an electrical connection to said electrode;
   an adhesive pad in adhesive contact with one said of said electrode;
   a gel pad in contact with the other side of the electrode and extending slightly beyond the inner and outer edges of the electrode so as to prevent direct contact by the electrode with the skin of a patient, said gel pad including a wholly enclosed interior aperture, said adheisve pad extending beyond the outer edge of said gel pad around the entire periphery thereto and extending over the interior aperture in the gel pad, said interior aperture in said gel pad corresponding in shape to the shape of the interior aperture of the electrode, and being of a size such as to ensure that when the electrode assembly is placed in contact with a patient's skin, said adhesive pad seals the electrode assembly both around the the periphery thereof and within said interior aperture of said gel pad to maintain said electrode assembly in firm contact with the skin of the patient.

2. A skin conducting electrode assembly as claimed in claim 1, wherein said electrode and said gel pad include a plurality of wholly enclosed interior apertures.

3. A skin conducting electrode assembly for use on a patient comprising, in combination,
   an electrode comprising a thin conductive plate having at least one wholly enclosed interior aperture therein;
   means for making an electrical connection to said electrode;
   a gel pad in contact with one side of said electrode and extending beyond the edges of said electrode to prevent direct contact of said electrode with the skin of the patient, said gel pad having at least one wholly enclosed interior aperture corresponding in shape to the shape of said at least one wholly enclosed interior aperture in said electrode;

an adhesive pad in adhesive contact with the other side of said electrode, said adhesive pad extending beyond the outer edges of said gel pad around the entire periphery thereof and over said gel pad aperture;

the said at least one wholly enclosed interior aperture in said electrode and said at least one wholly enclosed interior aperture in said gel pad being sufficiently large to ensure that when the electrode assembly is placed in contact with a patient's skin, said adhesive pad seals the electrode assembly both around the periphery thereof and within said at least one interior aperture in said electrode and said at least one interior aperture in said gel pad so as to maintain said gel pad and said electrode in firm contact with the skin of the patient.

4. A skin conducting electrode assembly as claimed in claim 3, wherein said thin conductive plate and said gel pad each have a plurality of wholly enclosed interior apertures therein.

5. A skin conducting electrode assembly as claimed in claim 3, wherein said electrode is circular shaped and said aperture in said electrode is circular shaped.

6. A skin conducting electrode assembly as claimed in claim 5, wherein the inside diameter of said electrode aperture is 1/20 or more of the outside diameter of said electrode.

7. A skin conducting electrode assembly as claimed in claim 3, wherein said adhesive pad has an orifice therein, and said electrical connection means comprises a conductive, one-piece stud fixedly mounted on said electrode and extending through said orifice in said adhesive pad.

* * * * *